(12) United States Patent
Allen et al.

(10) Patent No.: US 7,316,711 B2
(45) Date of Patent: Jan. 8, 2008

(54) INTRALUMENAL STENT DEVICE FOR USE IN BODY LUMENS OF VARIOUS DIAMETERS

(75) Inventors: Jeffrey Allen, Santa Rosa, CA (US); Mark Dolan, Santa Rosa, CA (US); Richard Thomas, Cloverdale, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 611 days.

(21) Appl. No.: 10/694,723

(22) Filed: Oct. 29, 2003

(65) Prior Publication Data

US 2005/0096727 A1    May 5, 2005

(51) Int. Cl.
*A61F 2/06* (2006.01)
(52) U.S. Cl. .................................... 623/1.15
(58) Field of Classification Search ......... 623/1.3–1.35
See application file for complete search history.

(56) References Cited

U.S. PATENT DOCUMENTS

| | | | |
|---|---|---|---|
| 4,580,568 A | 4/1986 | Gianturco | |
| 4,733,665 A | 3/1988 | Palmaz | |
| 5,195,984 A | 3/1993 | Schatz | |
| 5,292,331 A | 3/1994 | Boneau | |
| 5,514,154 A | 5/1996 | Lau | |
| 5,591,197 A * | 1/1997 | Orth et al. | 623/1.16 |
| 5,876,432 A | 3/1999 | Lau | |
| 6,540,775 B1 | 4/2003 | Fischell et al. | |
| 6,706,061 B1 | 3/2004 | Fischell et al. | |
| 6,790,227 B2 * | 9/2004 | Burgermeister | 623/1.15 |
| 7,141,062 B1 * | 11/2006 | Pinchasik et al. | 623/1.15 |
| 2002/0007211 A1 | 1/2002 | Pinchasik et al. | |
| 2003/0028240 A1 | 2/2003 | Nolting et al. | |
| 2003/0045926 A1 | 3/2003 | Pinchasik | |
| 2004/0093073 A1 * | 5/2004 | Lowe et al. | 623/1.15 |

FOREIGN PATENT DOCUMENTS

| | | |
|---|---|---|
| EP | 1 129 673 A3 | 9/2001 |
| WO | WO 01/64133 A1 | 9/2001 |
| WO | WO 03/022172 | 3/2003 |

\* cited by examiner

*Primary Examiner*—Anhtuan T. Nguyen
*Assistant Examiner*—Elizabeth Houston

(57) ABSTRACT

The present invention is an intralumenal stent device made up of two or more elements. Each element has undulations forming peaks and valleys and is formed from a repeating series including a long segment, a first midsized segment, a short segment, and a second midsized segment. These elements are aligned on a common axis and are connected directly to an adjacent element by a connection. The stent incorporates the advantages of having both long and short segments into a single element.

8 Claims, 8 Drawing Sheets

INTRALUMENAL STENT DEVICE FOR USE IN BODY LUMENS OF VARIOUS DIAMETERS

FIELD OF THE INVENTION

The present invention is directed to intralumenal stents for use in maintaining open collapsed lumen walls of various diameters.

BACKGROUND OF THE INVENTION

A wide range of medical treatments have been previously developed using "endoluminal prostheses," which terms are herein intended to mean medical devices which are adapted for temporary or permanent implantation within a body lumen, including both naturally occurring or artificially made lumens. Examples of lumens in which endoluminal prostheses may be implanted include, without limitation: arteries, such as those located within the coronary, mesentery, peripheral, or cerebral vasculature; veins; gastrointestinal tract; biliary tract; urethra; trachea; hepatic shunts; and fallopian tubes. Various types of endoluminal prostheses have also been developed, each providing a uniquely beneficial structure to modify the mechanics of the targeted luminal wall.

For example, stent prostheses have been previously disclosed for implantation within body lumens. Various stent designs have been previously disclosed for providing artificial radial support to the wall tissue, which forms the various lumens within the body, and often more specifically within the blood vessels of the body.

Cardiovascular disease, including atherosclerosis, is the leading cause of death in the U.S. The medical community has developed a number of methods and devices for treating coronary heart disease, some of which are specifically designed to treat the complications resulting from atherosclerosis and other forms of coronary arterial narrowing.

One method for treating atherosclerosis and other forms of coronary narrowing is percutaneous transluminal coronary angioplasty, commonly referred to as "angioplasty," "PTA" or "PTCA". The objective in angioplasty is to enlarge the lumen of the affected coronary artery by radial hydraulic expansion. The procedure is accomplished by inflating a balloon of a balloon catheter within the narrowed lumen of the coronary artery. In some instances the vessel restenoses chronically, or closes down acutely, negating the positive effects of the angioplasty procedure.

To provide radial support to the treated vessel in order to prolong the positive effects of PTCA, a stent may be implanted in conjunction with the procedure. Effectively, the stent overcomes the natural tendency of the vessel walls of some patients to close back down, thereby maintaining a more normal flow of blood through that vessel than would be possible if the stent were not in place. Under this procedure, the stent may be collapsed to an insertion diameter and inserted into a body lumen at a site remote from the diseased vessel. The stent may then be delivered to the desired site of treatment within the affected lumen and deployed to its desired diameter for treatment.

Access to a treatment site is most often reached from the femoral artery. A flexible guiding catheter is inserted through a sheath into the femoral artery. The guiding catheter is advanced through the femoral artery into the iliac artery and into the ascending aorta. Further advancement of the flexible catheter involves the negotiation of an approximately 180 degree turn through the aortic arch to allow the guiding catheter to descend into the aortic cusp where entry may be gained to either the left or the right coronary artery, as desired. Because the procedure requires insertion of the stent at a site remote from the site of treatment, the device must be guided through the potentially tortuous conduit of the body lumen to the treatment site. Therefore, the stent must be capable of being reduced to a small insertion diameter and must be flexible.

An example of a stent that displays high radial strength includes, but is not limited to, the undulating stent disclosed in U.S. Pat. No. 5,292,331 to Boneau, the disclosure of which is herein incorporated by reference. Other examples of undulating stents include but are not limited to those disclosed in U.S. Pat. No. 4,580,568 issued to Gianturco, U.S. Pat. No. 4,733,665 issued to Palmaz, U.S. Pat. No. 5,195,984 issued to Schatz, or U.S. Pat. No. 5,514,154 issued to Lau. For example, the Gianturco stent generally has long undulations, while the Schatz and Lau stents generally have smaller undulations. However, in each case, these designs have undulations of the same length.

Once an undulating stent is positioned across the lesion, it is expanded. As it expands, straight portions of undulations, or segments, move apart, such that the segment, turn, segment angle increases. As the angle increases, the length of the overall stent tube contracts and the diameter expands. This foreshortening of the longitudinal length of the stent makes it difficult to ensure that a particular undulating stent will be long enough to cover the lesion effectively when expanded.

Further, various characteristics become important when the stent is expanding to a small diameter versus when it is expanded to a larger diameter. For instance, a stent designed for use in a larger vessel would likely have insufficient radial strength at a smaller diameter. Similarly, a stent designed for use is smaller vessels would suffer from excessive foreshortening, bunching and reduced scaffolding if used at a larger diameter.

Thus, it is desirable to have an interlumenal stent device, which provides improved radial strength, scaffolding and flexibility, without foreshortening or bunching when expanded to a variety of larger and smaller diameters.

BRIEF SUMMARY OF THE INVENTION

The present invention is directed to an intralumenal stent device that solves many of the problems that occur when a stent is used in vessels of various diameters. In particular, the stent of the present invention uses a combination of short and long segments to obtain the benefits of each. In the present invention, rather than a series of short and long segments located substantially in the same place, the stent of the present invention has long and short segments dispersed throughout the stent body by incorporating long and short segments into each undulating element.

In one embodiment, the stent has generally undulating elements connected together. Each element has a repeating pattern of undulations formed from long, short and medium sized segments connected together by hairpin turns. The hairpin turns form peaks and valleys of the stent, by which adjacent stents may be connected. In one particular embodiment, the repeating pattern is a series that includes a long segment and a first midsized segment coupled by a first peak turn. The first midsized segment is coupled to a short segment by a first valley turn. The short segment and a second midsized segment are coupled by a second peak turn, and the second midsized segment is coupled to the next series by a second valley turn. The combination of short, midsized, and long segments provide the benefits provided by elements having different length segments combined into one stent design.

In one embodiment, adjacent elements are aligned such that shorter valleys are aligned with longer peaks. Shorter peaks and shorter valleys may have a larger turn radius that those for longer peaks and longer valleys. The larger turn radius provides less resistance to expansion than a larger radius.

Elements may be connected together where the peak and valleys meet, such that a first peak turn of an element may be connected to a first valley turn of an adjacent element. Also, a second peak turn of an element may be connected to a second valley turn of an adjacent element.

Adjacent elements may be formed from a toroid bent into the particular pattern. Thus, each element may be connected to an adjacent element by welding (or another mechanical type of connection) the peaks and valleys to each other. Alternatively, the elements may be formed connected as a unitary structure.

The elements may be placed onto a balloon of a balloon catheter for expansion within a body lumen or they may naturally occur in an expanded condition and may be collapsed, reducing the overall profile for delivery. Once at the treatment site, the stent may be expanded to its natural condition.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE FIGURES

The accompanying drawings, which are incorporated herein and form a part of the specification, illustrate the present invention and, together with the description, further serve to explain the principles of the invention and to enable a person skilled in the pertinent art to make and use the invention.

DETAILED DESCRIPTION OF THE INVENTION

Figure 1A:
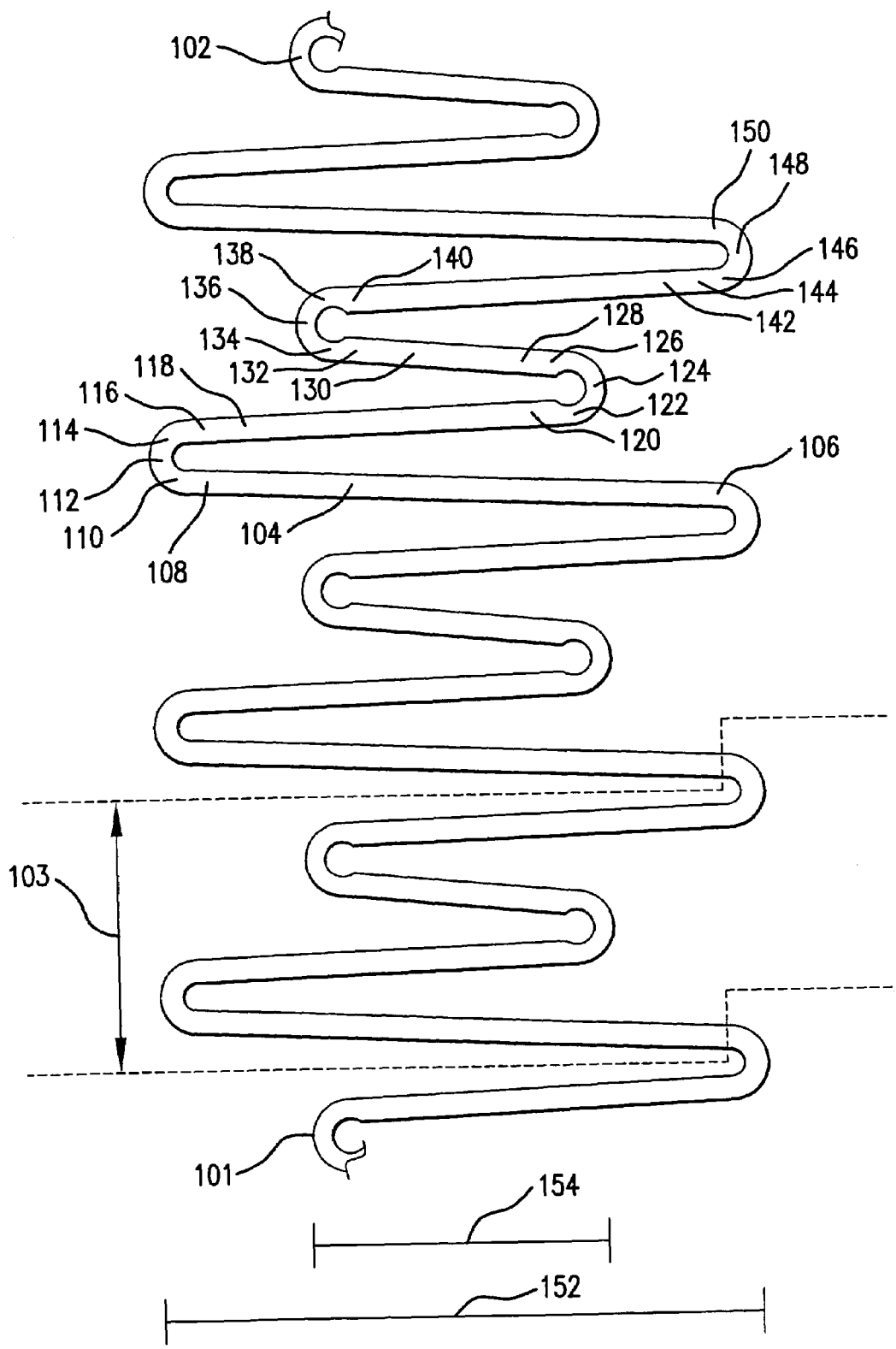
FIG. 1a is a plan view of a flattened element of the present invention.

The present invention will be described with reference to the accompanying drawings. The drawing in which an element first appears is typically indicated by the leftmost digit(s) in the corresponding reference number.

Figure 1B:
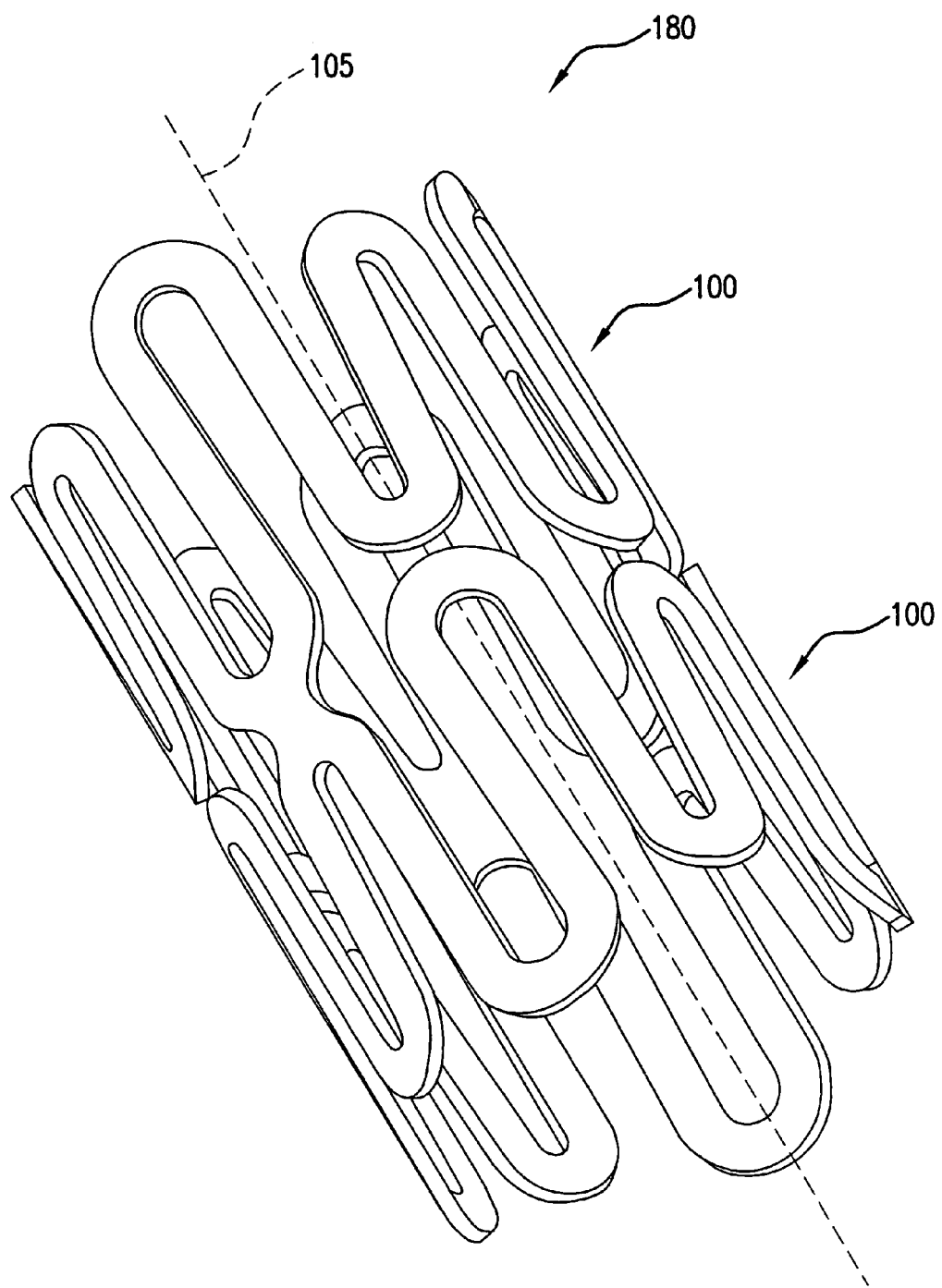
FIG. 1b is a three-dimensional perspective view of a stent of the present invention.

The present invention generally is directed to a stent made from generally circular single elements having a uniquely defined undulating shape. Elements are aligned on a common longitudinal axis to form a generally cylindrical body having a radial and longitudinal axis. FIG. 1a shows a single element 100 of the present invention. Element 100 is shown in a schematic, as if the generally circular element 100 has been cut between ends 101 and 102 and the element 100 has been laid out flat. FIG. 1b shows a perspective view of a stent of the present invention having two elements 100 positioned around a longitudinal axis 105, which defines a longitudinal direction.

FIG. 1b shows element 100 appearing flat, as if made from a ribbon bent into a sinusoidal shape. One skilled in the art can appreciate that an element 100 of the present invention may be manufactured in a variety of ways, which are discussed in further detail below. Thus, element 100 may be made flat, as shown in FIG. 1b, rounded, elliptical, or have a variety of other cross-sections depending upon the desired features of the stent. Thus, a stent of the present invention is not limited to the ribbon structure shown in FIG. 1.

The generally cylindrical elements and stents are shown in FIGS. 2-7 in a flattened state, such as the element 100 shown in FIG. 1a. However, one skilled in the art can appreciate that the stents and/or elements depicted therein are intended to be used in a cylindrical body, such as that shown in FIG. 1b.

When viewed flat, each element 100 is an undulating wire having a repeating pattern in the amplitudes of each undulation. These amplitudes are formed from a repeating series 103 of segments and turns. In a preferred embodiment, element 100 is formed from a closed toroid wire which is bent into the structure shown in FIG. 1a. Thus, segments and turns are not necessarily coupled together at the ends, but are naturally continuing one into another. Other embodiments may be manufactured differently, such that some portions may be mechanically coupled together via welding, soldering, adhesive or another bonding or another mechanical connection method. However, to described the particular structure of element 100, various segments and turns may be described as being connected or coupled to each other. Thus, the terms "connect with," "connected," or "coupled" may mean either naturally continuing (or flowing together) or mechanically coupled together.

The series 103 includes a long segment 104. Long segment 104 connects with the previous series 103 at a first end 106. A second end 108 of long segment 104 connects with a first end 110 of a first peak turn 112. A second end 114 of first peak turn 112 connects with a first end 116 of a first midsized segment 118. First midsized segment 118 is shorter than long segment 104. A second end 120 of first midsized segment 118 connects with a first end 122 of a first valley turn 124. First valley turn 124 faces the opposite longitudinal direction as first peak turn 112. For the purpose of this description, peaks and valleys may face either longitudinal direction provided that all peaks face one longitudinal direction and all valleys face the opposite longitudinal direction. Thus, when two elements are side by side, flipping one element in the opposite direction would by definition convert all the peaks to valleys and valleys to peaks.

A second end 126 of first valley turn 124 connects with a first end 128 of a short segment 130. Short segment 130 is shorter than midsized segment 118. A second end 132 of short segment 130 connects with a first end 134 of a second peak turn 136. Because short segment 130 is shorter than first midsized segment 118, second peak turn 136 does extend as far in the longitudinal direction as first peak turn 112.

A second end 138 of second peak turn 136 connects with a first end 140 of a second midsized segment 142. A second end 144 of midsized segment 142 connects with a first end 146 of a second valley turn 148. A second end 150 of second valley turn 148 connects with the next adjacent series 103. Because second midsize segment 142 is longer than short segment 130, first valley turn 124 does not extend as far in the longitudinal direction as second valley turn 148.

Thus, element 100 has regions of shorter segments 154 and regions of longer segments 152 within the same circular element 100. A stent having both of these regions can be used in body vessels of various sizes by using the advantages of having both short and long segments.

For example, a stent that performs well in a vessel having a larger diameter would likely have insufficient radial strength when placed in a vessel having a smaller diameter. Similarly, a stent designed for use in a vessel having a smaller diameter would likely suffer from foreshortening, bunching and reduced scaffolding when used in a vessel of a larger diameter.

Generally, radial strength increases with a decrease in segment size. The segments create a wider angle when they expand. A wider angle provides more strength because it takes more force to close a wider angle than a smaller one. Consequently, smaller segments do not radially recoil as easily as larger segments, when expanded. However, shorter segments are less flexible. Larger segments will flex and allow the element 100 to be flexible to better curve around tortuous vessels.

Foreshortening occurs upon expansion. As element 100 radially expands, the segments pivot away from each other forming larger angles the greater the stent expands. As the segments pivot, the overall longitudinal distance between a peak and a valley is shortened. Longer segments have less shortening than smaller segments because the overall longitudinal distance between the peaks and valleys does not change as dramatically upon expansion.

Generally, a balloon expands first on its ends. As the ends begin to expand, the balloon begins to form a "dog bone" shape (i.e., unexpanded in the middle and expanded on both ends). The larger ends put force on the elements in a longitudinal direction towards the middle of the stent. Shorter segments are more susceptible to this force. Elements on the ends begin to pile on top of one another causing bunching, or "trainwrecking". Longer segments are not as susceptible to the force and hold their position better on the balloon.

Smaller segments also create greater scaffolding than larger segments. Greater scaffolding means that more area of the vessel walls is being supported directly by parts of the stent. Smaller segments and more turns cause more area of the lumen walls to contact parts of the stent.

Thus, for a stent designed for any vessel size, a trade off occurs when only longer or only shorter segments are used. The present invention solves these problems and makes the stent suitable for a wider range of vessel sizes. The shorter segments 154 provide greater radial support at low diameters, increasing radial strength and minimizing recoil. At larger diameters, the longer segments 152 enhance the radial strength of the smaller segments 154. Further, smaller segments 154 decrease cell size (i.e., increase scaffolding), while longer segments 152 enhance flexibility of each element 100. Longer segments 152 also minimize bunching and foreshortening of the stent upon expansion. Thus, the combination of longer and shorter segments 152, 154, combine the benefits of each into element 100. When elements 100 are connected together (as discussed below), these benefits are also spread out over the longitudinal length of the stent.

The distance between second valley turn 148 and first valley turn 124 may be increased or decreased depending on the length of midsized segment 142. Preferably, in a preferred embodiment, first and second midsized segments 118 and 142 are the same length. However, in other embodiments, second midsized segment 142 may be longer or shorter than first midsized segment 118.

Preferably each series 103 is identical to the adjacent series 103. However, one skilled in the art can appreciate that each series 103 may have different sized long segments 104, first and second midsized segments 118 and 142 and short segments 130 from the series 103 that is before or after it. However, the lengths of the long segments 104, first and second midsized segments 118, 142 and short segments 130 become particularly important when more than one element 100 is aligned on a common axis, as discussed with respect to FIG. 2 below.

FIG. 1a shows element 100 having four full series 103. However, any number of series 103 may be used in element 100. For example, when element 100 is to be used in body lumens having large diameters, more series 103 may be used. Meanwhile, as few as two series 103 may be used in an element 100 for use in body lumens with small diameters.

In general, long segment 104 and short segment 130 are parallel and first and second midsized segments 118 and 142 are parallel. In FIG. 1a, long segment 104 and short segment 130 generally lean to the right, while first and second midsized segments 118 and 142 lean generally to the left. However, long segments 104 and short segment 130 may lean generally to the left, while first and second midsized segments 118 and 142 lean generally to the right, such as series 203 of element 200 as shown and described in FIG. 2.

Figure 2:
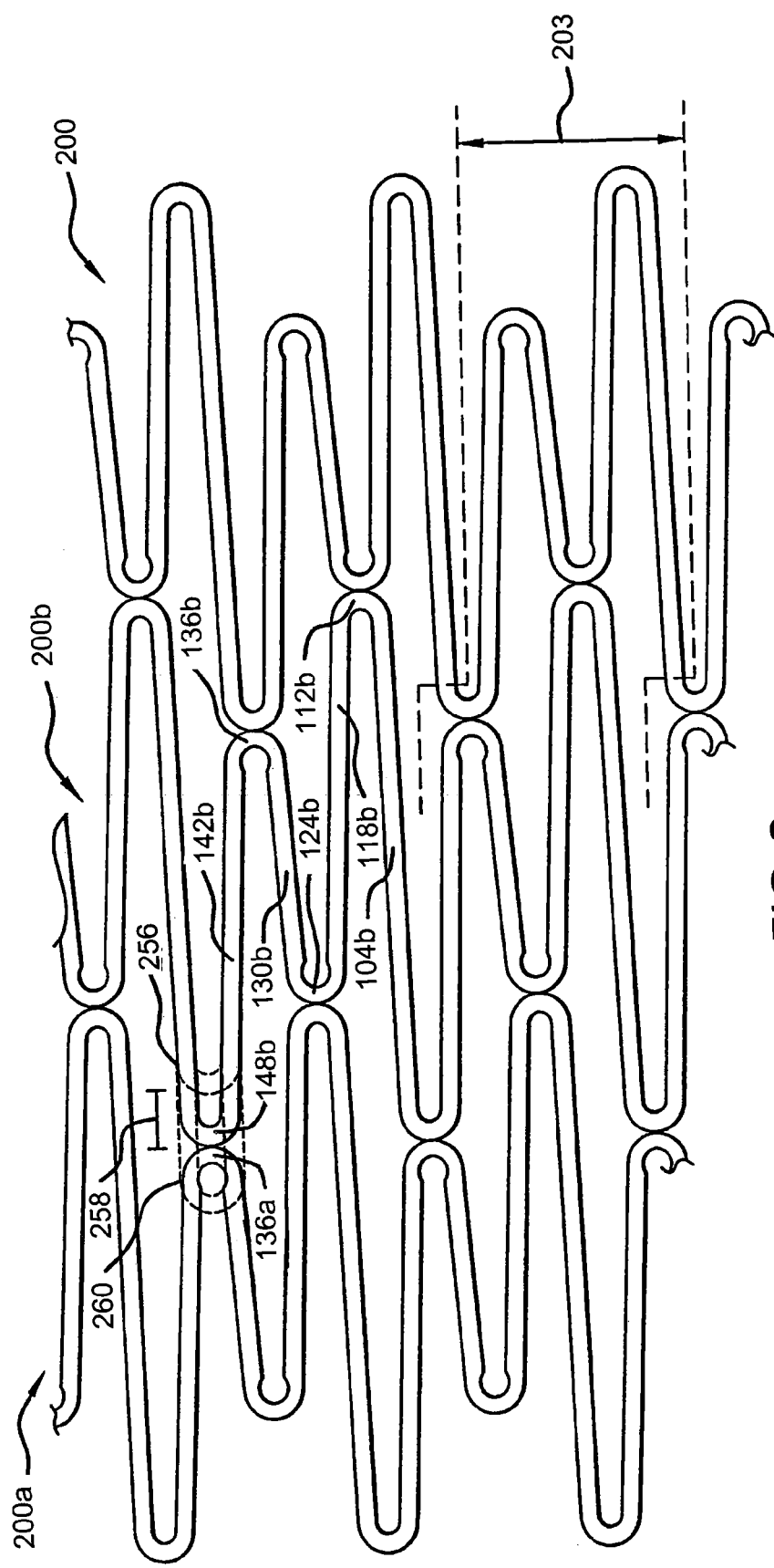
FIG. 2 is a plan view of flattened aligned elements of the present invention.

As discussed above, the particular length of the segments becomes significant when the elements 200 are aligned on common longitudinal axis. FIG. 2 shows how elements 200a, 200b maybe aligned when each long segment 104a, 104b is the same length, each first and second midsized segments 118a, 118b, 142a, 142b are the same length and each short segment 130a, 130b is the same length. In this embodiment, shorter peaks of an element fit with longer valleys of an adjacent element, and longer peaks of an element fit with shorter valleys of an adjacent element. In other words, first peak turn 112a abuts first valley turn 124b of an adjacent element and second peak turn 136a abuts second valley turn 148b of an adjacent element.

Figure 3:
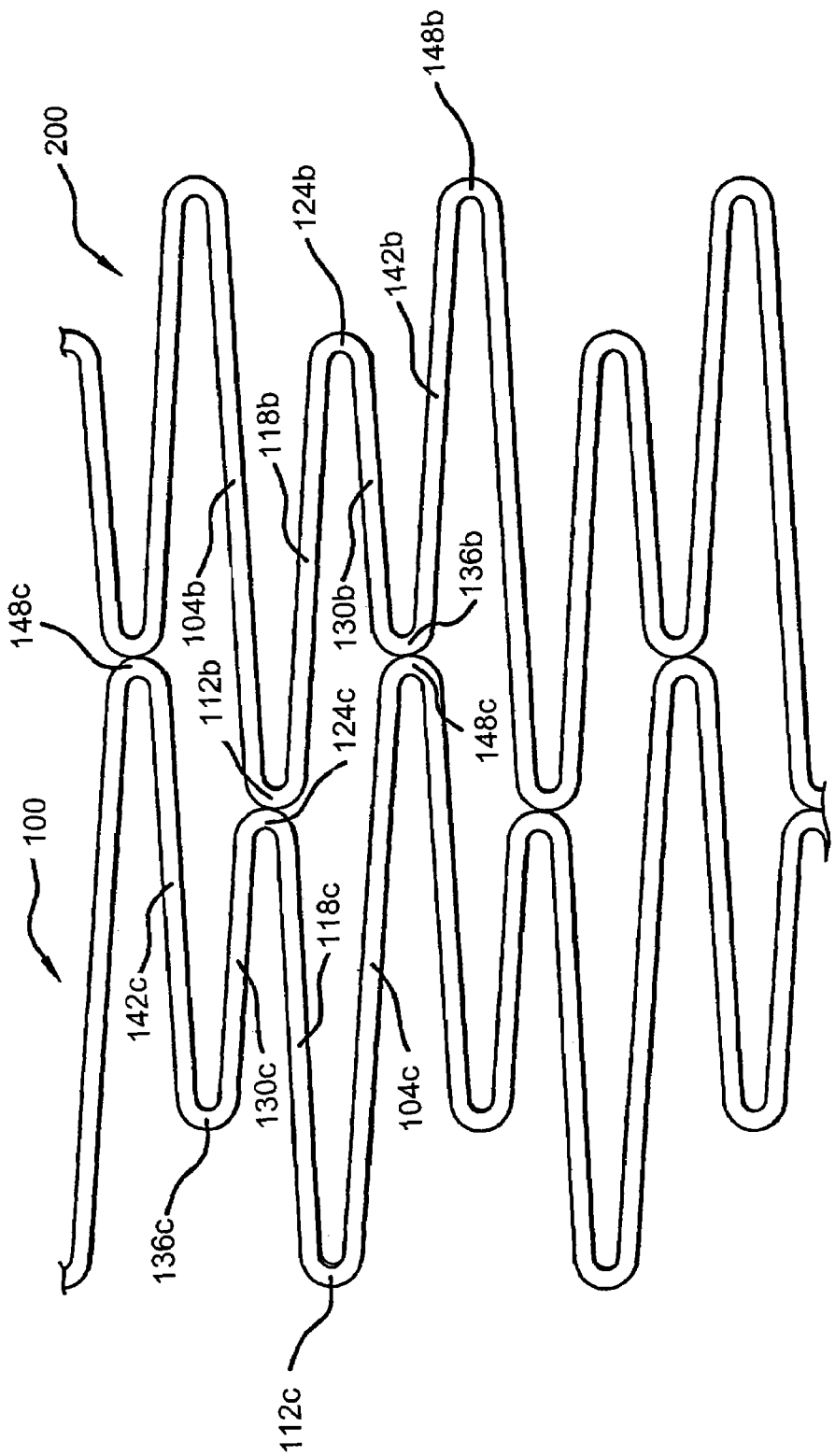
FIG. 3 is another plan view of flattened aligned elements of the present invention.

Elements 100 and 200 are functionally the same. The alignment of elements 100 of FIG. 1 would be a mirror image of the alignment of elements 200 of FIG. 2. Alternatively, elements 100 and 200 may be aligned together, such as in alternating bands, as shown in FIG. 3. In FIG. 3, the alignment still has first peak turn 12b abutting first valley turn 124c and second peak turn 136b abutting second valley turn 148c. Thus, one skilled in the art can appreciate that any arrangement of elements 100 and 200 may be suitable for the stent of the present invention.

If second midsized segment 142b is shorter than first midsized segment 118b (as shown in phantom lines 256 in FIG. 2), second valley turn 148b is located such that a gap 258 occurs between second valley turn 148b of a first element 200b and second peak turn 136a of the adjacent element 200a. Such gaps 258 reduce scaffolding and reduce support. Alternatively, if second midsized segment 142b is longer than first midsized segment 118b (as shown in phantom lines 260), second valley turn 148b of the first element 200b overlaps second peak turn 136a of the adjacent element 200a. Overlap may reduce the smooth effect of the stent causing turbulence in the vessel, which may lead to thrombosis. Therefore, unless all long segments 104b are the same length, all first and second midsized segments 118b, 142b are the same length and all short segments 130b are the same length, respectively, then adjustments must be made in the adjacent element 200a in order to keep peaks and valleys generally abutting one another.

Figure 4:
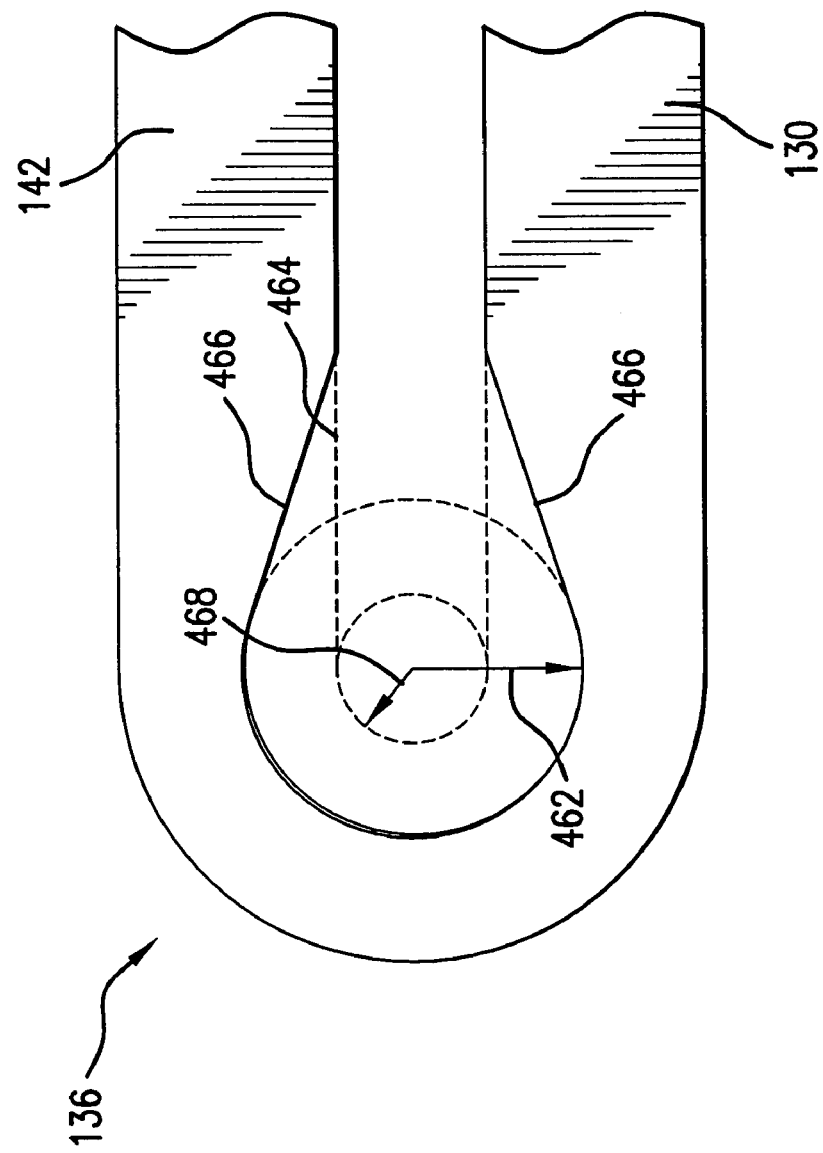
FIG. 4 is a detailed view of a turn of an element of the present invention.

FIG. 4 shows a detailed view of second peak turn 136 from FIG. 1a. First valley turn 124 and second peak turn 136 are similar in FIGS. 1a and 2 in that they have a larger turn radius 462 than first peak turn 112 and second valley turn 148. Thus, a detailed view of first valley turn 124 would be similar to FIG. 4. Phantom line 464 indicates where the thickness of the wire at the turn is consistent with the thickness of the wire at short segment 130 and second midsized segment 142. However, second peak turn 136 has sloping walls 466 that reduce the thickness of the wire at the turn. Thus, the turning radius 462 is larger than a standard radius 468, which is the turn radius of first peak turn 112 and second valley turn 148.

Longer segments 152 expand easier than shorter segments 154 because, as the length increases, the segment has less resistance to angular rotation. Consequently, longer segments 152 will expand before shorter segments 154. Thus, the advantage of shorter segments discussed above will be lost when the shorter segments do not expand. However, a larger turn radius 462 provides less resistance to expansion. Thus, first valley turn 124 and second peak turn 136, which bracket short segment 130, each have a larger turn radius 462 to ensure that longer segments 152 and shorter segments 154 will expand uniformly.

A stent can be expanded in several ways. Some stents are collapsed from a natural expanded shape into a collapsed state for delivery to the vessel. When a sleeve holding the stent in the collapsed shape is removed, the stent expands to its natural expanded state in the correct position within the lumen. Other stents are heat expandable. Once placed in the correct position, the stent is subjected to a heat source, which causes the expansion of the stent through a chemical reaction or natural thermal expansion, depending upon the material from which the stent is made. Still other stents are collapsed on top of a balloon, such as the type of balloon used in an angioplasty procedure. As the balloon expands, it physically forces the stent to expand at the same time. The balloon is then collapsed leaving the stent in the expanded position.

Preferably, the stent of the present invention is formed in a natural state, crimped onto a balloon dilation catheter and expanded by the radial force of the balloon. However, one skilled in the art can appreciate that the stent of the present invention can be adapted for any type of delivery method.

The stent is preferably constructed of implantable materials having good mechanical strength. For example, a stent of one embodiment may be machined from implantable quality stainless steel bar stock. In another embodiment, a stent of the present invention could be made of any other metal suitable for implantation, such as cobalt based alloys (605L, MP35N), titanium, tantalum, superelastic nickel-titanium alloy, other biocompatible metals or thermoplastic polymers. Finally, although not required in all cases, the outside of the stent may be selectively plated with platinum to provide improved visibility during fluoroscopy.

Stents of the present invention may be formed using any of a number of different methods. For example, the stents may be formed by winding a wire or ribbon around a mandrel to form the pattern described above and then welding or otherwise mechanically connecting two ends thereof to form elements 100 or 200. Elements 100 or 200 are subsequently connected together to form the stent body. Alternatively, stents may be manufactured by machining tubing or solid stock material into toroid bands, and then bending the bands on a mandrel to form the pattern described above. Elements 100 or 200 formed in this manner are subsequently connected together to form the longitudinal stent body. Laser or chemical etching or another method of cutting a desired shape out of a solid stock material or tubing may also be used to form stents of the present invention. In this manner, elements 100 or 200 may be formed connected together such that the stent body is a unitary structure. Further, a stent of the present invention may be manufactured in any other method that would be apparent to one skilled in the art. The cross-sectional shape of the finished stent may be circular, ellipsoidal, rectangular, hexagonal rectangular, square, or other polygon, although at present it is believed that circular or ellipsoidal may be preferable.

Figure 5:
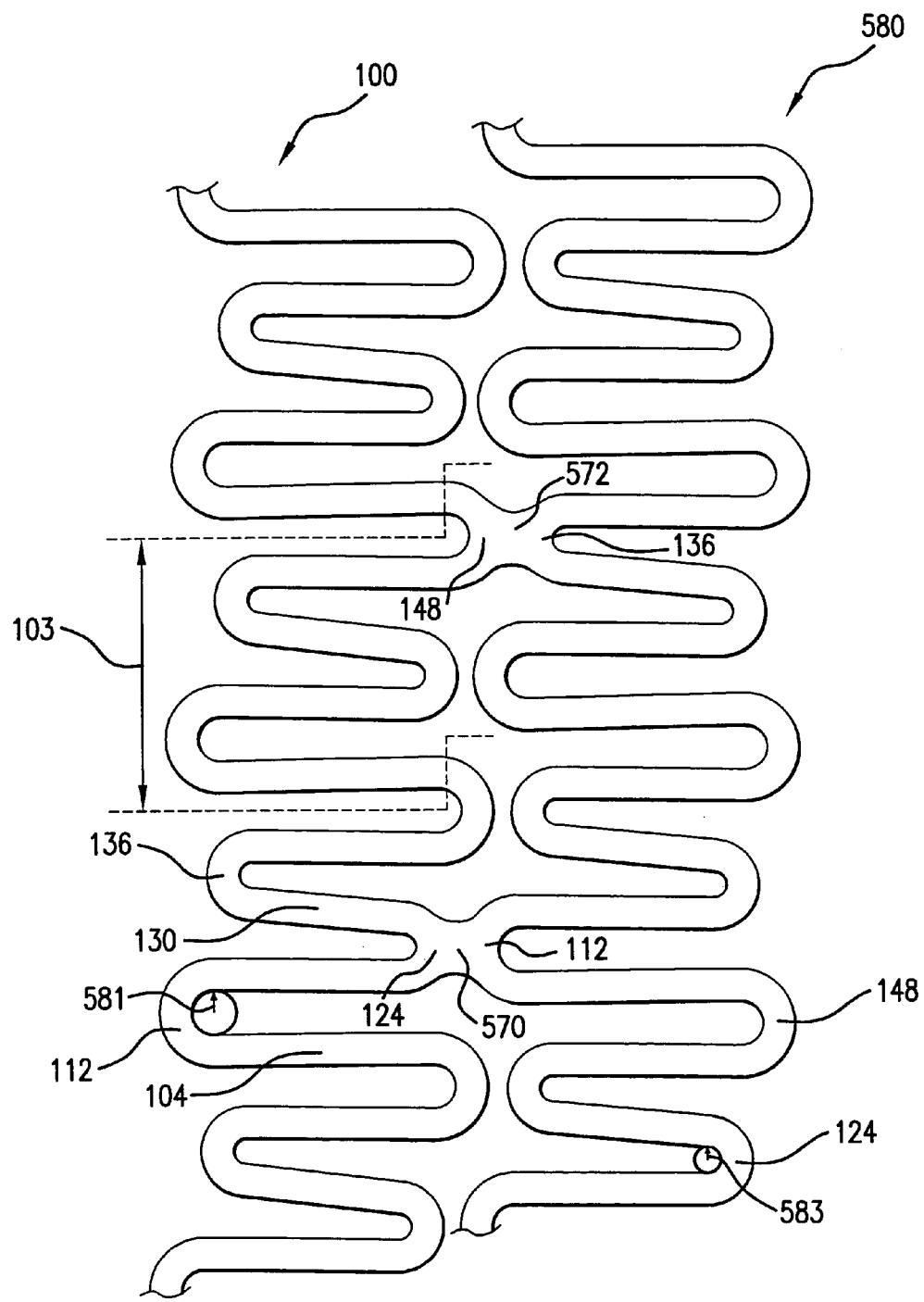
FIG. 5 is a detailed view of a flattened stent with connections between adjacent elements.

In the embodiment shown in FIG. 5, elements 100 are shown with first peak turn 112 and second valley turn 148 having a larger turn radius 581 than smaller turn radius 583 of first valley turn 124 and second peak turn 136. In this embodiment, larger turn radius 581 is not formed by making the thickness of the wire smaller, as discussed with respect to FIG. 4. Instead, larger turn radius 581 is made larger by forming the turn wider when bent by a form tool. Note that changing the radius of the turns in this manner may cause the orientation of the segments to change, in that long segment 104 is no longer generally parallel with short segment 130. Thus, other embodiments in which various turns have a different radius are encompassed by the present invention.

FIG. 5 shows a stent 580 having only two elements 100 connected at connections 570 and 572. Connection 570 is between first peak turn 112 of one element and first valley turn 124 of the adjacent element. Likewise, connection 572 is between second peak turn 136 of a first element and second valley turn 148 of the adjacent element. Connections 570 and 572 are preferably located where the peaks and valleys are welded together, such as by resistance welding, friction welding, laser welding or another form of welding such that no additional materials are used to connect elements 100. Alternatively, elements 100 can be connected by soldering, by the addition of a connecting element between the peaks and valleys, or by another mechanical method. Further, as discussed above, stent 580 may be formed pre-connected as a unitary structure, such as by laser cutting or etching the entire stent body from a hollow tube or sheet. Other connections or ways to connect elements would be apparent to one skilled in the art and are included herein. For example, FIG. 7, discussed in detail below shows another type of connection between adjacent elements 100.

In FIG. 5, connections 570 and 572 are spaced three turns apart. In other words elements 100 have two abutting peaks and valleys disposed between connections 570 and 572. However, connections 570 and 572 can be spaced any distance apart from one another. Further, connections 570 and 572 need not be placed directly at the peaks and valleys, but may occur anywhere on long segments 104, midsized segments 118, 142 or short segments 130. In yet another embodiment, any number of connections 570 and 572 can connect elements 100. For example, connections 570, 572 may be everywhere where peaks and valleys abut. Alternatively, elements 100 may not be connected, but may be implanted in the vessel aligned in this arrangement without being physically connected.

Figure 6:
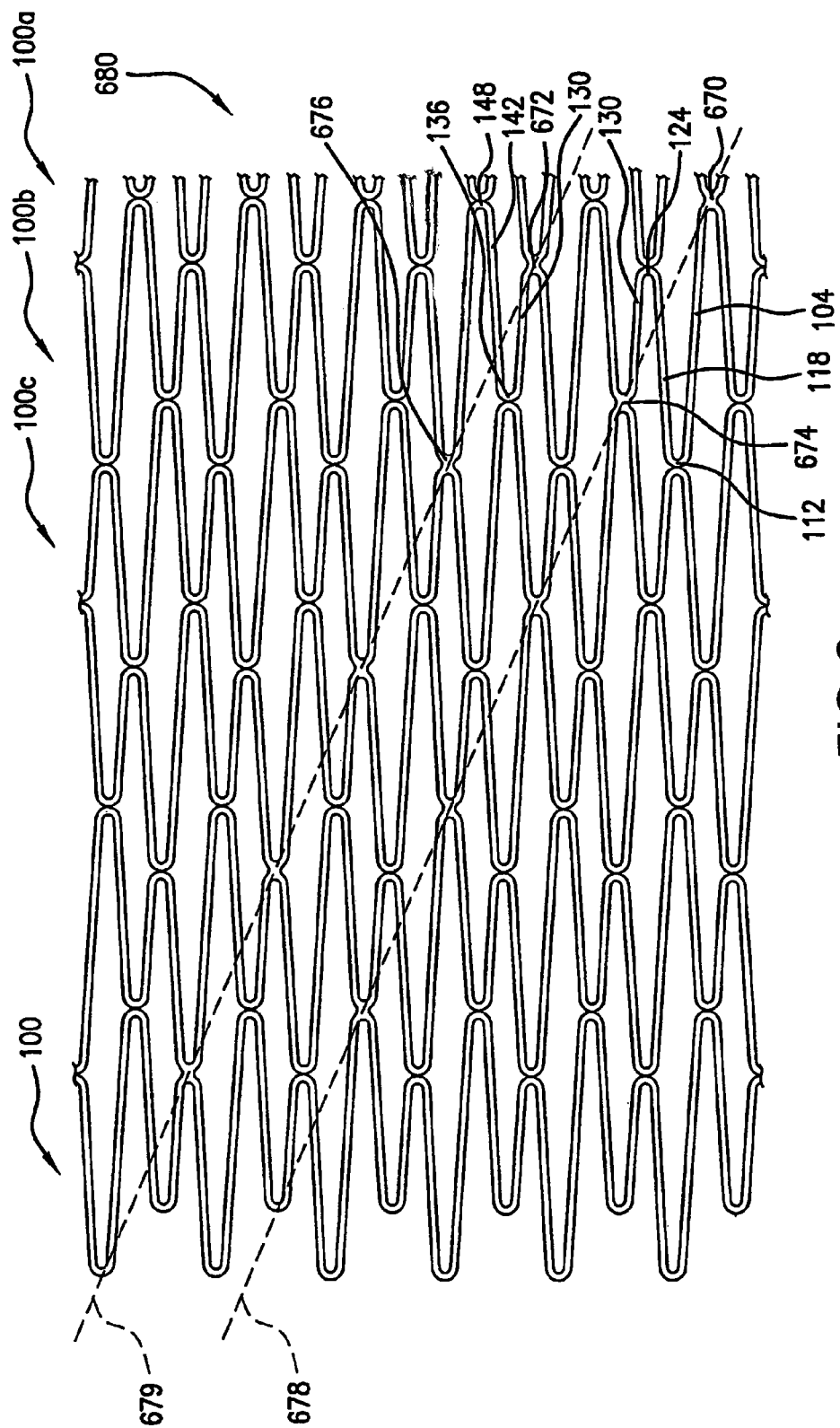
FIG. 6 is a plan view of another flattened stent of the present invention with connections between adjacent elements.

FIG. 6 shows stent 680 having more than two elements 100 connected together. Stent 680 can have any number of elements 100. In a preferred embodiment, subsequent pairs of elements 100 are connected at a location that is circumferentially displaced from the previous pair. For example, a portion of a first element 100a is shown in FIG. 6 being connected to a second element 100b by connections 670 and 672. Second element 100b is connected to a third element 100c by connections 674 and 676. In FIG. 6, connections 674 and 676 are circumferentially displaced from connection 670 and 672 in each case by three segments and two turns. In other words, a long segment 104, a first peak turn 112, a first midsized segment 118, a first valley turn 124 and a short segment 130 are between connection 670 and connection 674. Similarly, a short segment 130, a second peak turn 136, a second midsized segment 142, a second valley turn 148 and a long segment 104 are between connection 672 and connection 674. Thus, a pattern formed by connections 670, 672, 674 and 676 is repeated along the longitudinal length of stent 680, as shown with phantom lines 678 and 679. The pattern generally forms a double helix shape, as the connections are displaced on the generally cylindrical shaped stent 680.

One skilled in the art would recognize that the pattern formed in FIG. 6 is only one possible way in which multiple elements can be connected. For example, connections 674 and 676 may be separated by more or less turns than connections 670 and 672. Also, connections 674 and 676 may be circumferentially displaced from connections 670 and 672 more or less than shown in FIG. 6. Further, there may be additional or fewer connections between first element 100a and second element 100b than there are between second element 100b and third element 100c. For example, each location where peaks and valleys abut may be connected, only one peak and one valley may be connected or no peaks and valleys may be connected. Finally, one skilled in the art can appreciate that elements 100 of the present invention can be connected by no pattern at all, i.e., in a random arrangement of connections.

Figure 7:
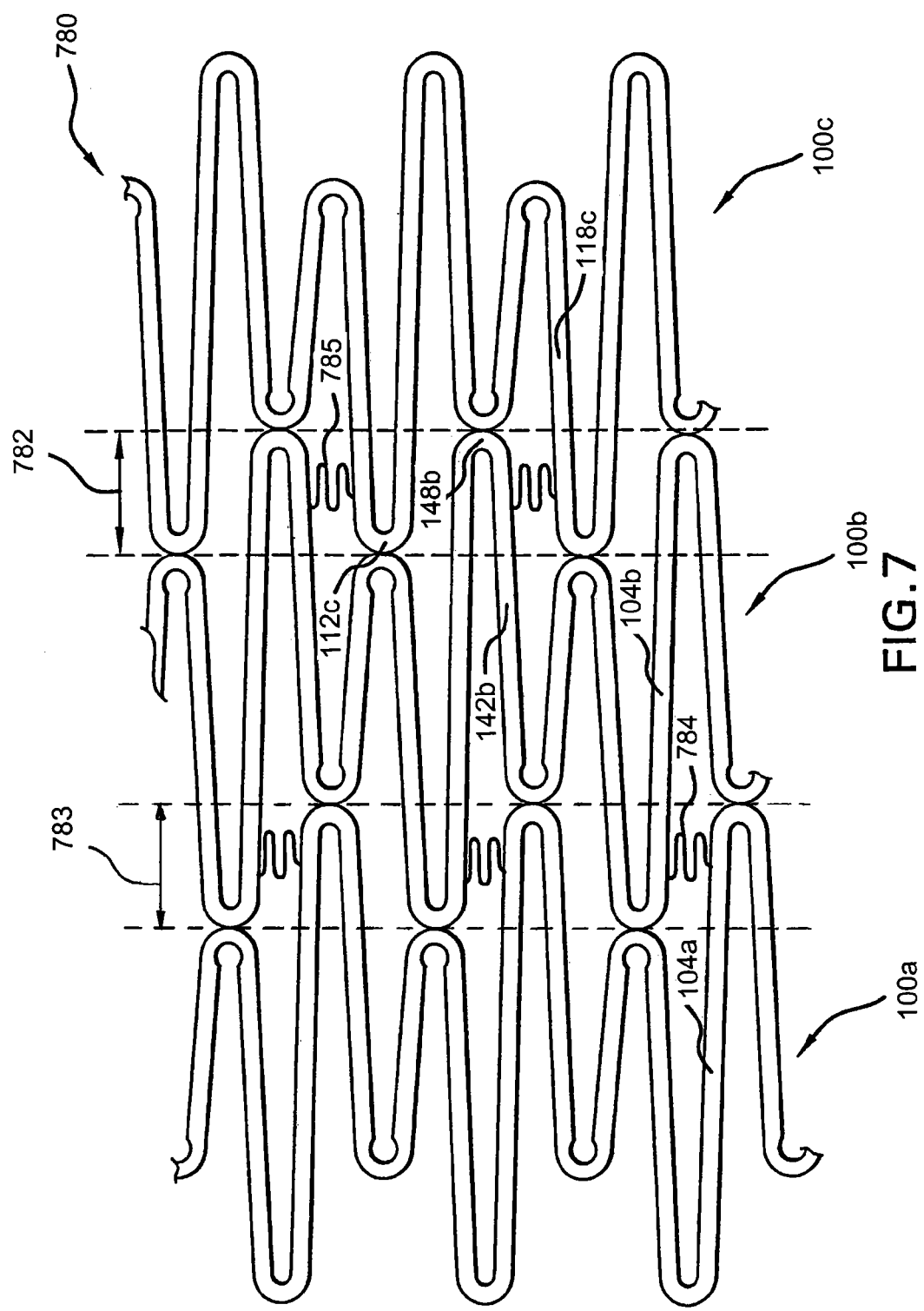
FIG. 7 is a detailed view of another flattened stent of the present invention with connections between adjacent elements.

FIG. 7 shows another way in which elements 100 or 200 can be connected. Elements 100b, 100c are aligned such that first peak turn 112c and second valley turn 148b overlap in region 782. In region 783 connection members 784 may extend between a long segment 104a of an element 100a and a long segment 104b of adjacent element 100b. Alternatively, a connection member 785 may extend between a first midsized segment 118c of an element 100c and a second midsized segment 142b of an adjacent element 100b. In an unexpanded condition, connection members 784,785 extend in a radial direction (i.e. perpendicular to a longitudinal direction), and thus do not create a longitudinal space between adjacent elements 100a, 100b, 100c.

Connection members 784, 785 may connect adjacent elements 100a, 100b, 100c alone or in combination with welded connections (such as connections 570 and 572 of FIG. 5). Further, connection members 784, 785 may be sinusoidal shaped, as shown in FIG. 7. However, connection members may be other shapes, such as straight, hinged, or any other shape that would be apparent to one skilled in the art, provided that they are capable of spanning in a radial direction between segments of adjacent elements 100a, 100b, 100c. However, it is preferred that connection members be sinusoidal shaped. Thus, as the segments (such as long segments 104a, 104b on either end of connection member 784) move apart from each other upon expansion of the stent, connection members will also expand. Sinusoidal shaped connection members may have as few as one turn or may have several turns bunched into a small area.

Connection members 784, 785 may be attached to one or more segments in a mechanical connection, such as by resistance welding, friction welding, laser welding or another form of welding, soldering or by another mechanical method. Further, connection members 784, 785 may be formed pre-connected as a unitary structure with the rest of stent 780, such as by laser cutting or etching the entire stent body from a hollow tube or sheet. Other connections or ways to connect elements would be apparent to one skilled in the art and are included herein.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. An intralumenal stent device, comprising: two or more elements aligned to form adjacent elements, each element having a similar pattern of undulations forming peaks and valleys, said pattern being formed from a repeating series including a straight long segment directly connecting with a first peak turn, said first peak turn being defined by a single turn radius, said first peak turn directly connecting with a first, straight midsized segment, said first midsized segment connecting with a first valley turn, said first valley turn connecting with a short segment, said short segment connecting with a second peak turn, said second peak turn connecting with a second midsized segment, said second midsized segment connecting with a second valley turn, said second valley turn connecting with a long segment of a similar adjacent series, wherein either at least one first peak turn of a first element is connected to a first valley turn of an adjacent second element or at least one second peak turn of a first element is connected to a second valley turn of an adjacent second element, wherein said elements are connected directly to adjacent said elements.

2. The intralumenal stent device of claim 1 wherein the first element has a first connection point and a second connection point with an adjacent element, said first connection point being from a first peak turn of the first element to a first valley turn of the second element and wherein said second connection point is from a second peak turn of the first element to a second valley turn of the second element.

3. The intralumenal stent device of claim 2, wherein said first and second connection points between said first element and a said second element are circumferentially displaced from first and second connection points between said second element and a third element, such that subsequent first and second connection points form a longitudinal double helix pattern.

4. The intralumenal stent device of claim 1, wherein said adjacent elements are connected by welding.

5. The intralumenal stent device of claim 1, wherein said adjacent elements are formed connected.

6. The intralumenal stent device of claim 1, wherein said elements are formed from a toroid.

7. The intralumenal stent device of claim 1, wherein said first valley turn and said second peak turn have a larger turn radius than that of said first peak turn and said second valley turn.

8. The intralumenal stent device of claim 1, wherein said two or more elements are placed onto a balloon of a balloon catheter for expansion within a body lumen.

* * * * *